United States Patent [19]
Millo

[11] Patent Number: 5,870,692
[45] Date of Patent: Feb. 9, 1999

[54] EFFLUENT MONITORING SYSTEM

[75] Inventor: Jean Millo, Ville Mont-Royal, Canada

[73] Assignee: Systemes Integres ABDMF Inc., Quebec, Canada

[21] Appl. No.: 794,634

[22] Filed: Feb. 3, 1997

[51] Int. Cl.[6] ............................................. A01J 5/01
[52] U.S. Cl. ................................. 702/45; 73/53.01
[58] Field of Search ............................ 364/509, 510, 364/569; 340/606, 603, 615, 618; 116/264, 273; 73/53.01, 53.04, 54.07, 152.18, 152.23, 861; 702/45

[56] References Cited

U.S. PATENT DOCUMENTS

| | | | |
|---|---|---|---|
| 5,091,863 | 2/1992 | Hungerford et al. | 364/510 |
| 5,646,863 | 7/1997 | Morton | 364/496 |

OTHER PUBLICATIONS

New, Improved 3010 Ultrasonic Flow Transmitter, Safe for Use in Hazardous Locations, 1994 Isco, Inc., Brochure No. 60-3403-201, U.S.A.

Isco 3240 Variable Gate Open Channel Flow Meter, Your Only Choice for Fluctuating Flows, 1993 Isco, Inc., Brochure No. 60-3243-186, U.S.A.

New Isco 4100 Series Flow Loggers, The Ultimate System for Multi-Site Flow Monitoring and Analysis, 1993 Isco, Inc., Brochure No. 60-3113-058, U.S.A.

Introducing Isco 4200 Series Flow Meters, Accurate Flow Measurement That's Versatile and Easy To Use, Brochure No. 60-3213-298, Second Printing 1996, U.S.A.

4501 Pump Station Flow Monitor, Isco, Inc., Brochure No. 60-4503-021, U.S.A.

Automate Your Voc Sampling, The Isco Model 6100 Sampler, 1996 Isco, Inc., Brochure No. 60-6003-145, Aug. 1996, U.S.A.

Isco Product Data, Isco Portable Peristaltic Pump, 1996 Isco, Inc., Brochure No. 1533DS, U.S.A.

UniMag from Isco, 1996 Isco, Inc., Brochure No. 60-4403-001, Aug. 1996, U.S.A.

Flowlink Software, Advanced Data Collection, Analysis and Reporting, 1995 Isco, Inc., Brochure No. 60-2453-132, U.S.A.

Isco Sampler Source Book, 1996 Isco, Inc., Catalog No. 60-9003-380, May 1996, U.S.A.

*Primary Examiner*—Thomas Peeso
*Attorney, Agent, or Firm*—Michael D. Bednarek; Kilpatrick Stockton LLP

[57] ABSTRACT

The effluent monitoring system generates an action perform signal for controlling a sampler device or an alarm in response to detecting a plurality of probe inputs receiving signals from a plurality of effluent property detecting probes. A variable and dynamic response to the probe inputs is provided. A plurality of monitoring parameter sets are stored in a memory along with a state number value, and the system may change state number in response to exceeding a threshold value which will result in the system being responsive to a new set of monitoring parameters in order to respond in a variable and dynamic manner. The sampling rate and the rate of recording values of the probe inputs can also be dynamically varied in response to the probe inputs themselves.

18 Claims, 8 Drawing Sheets

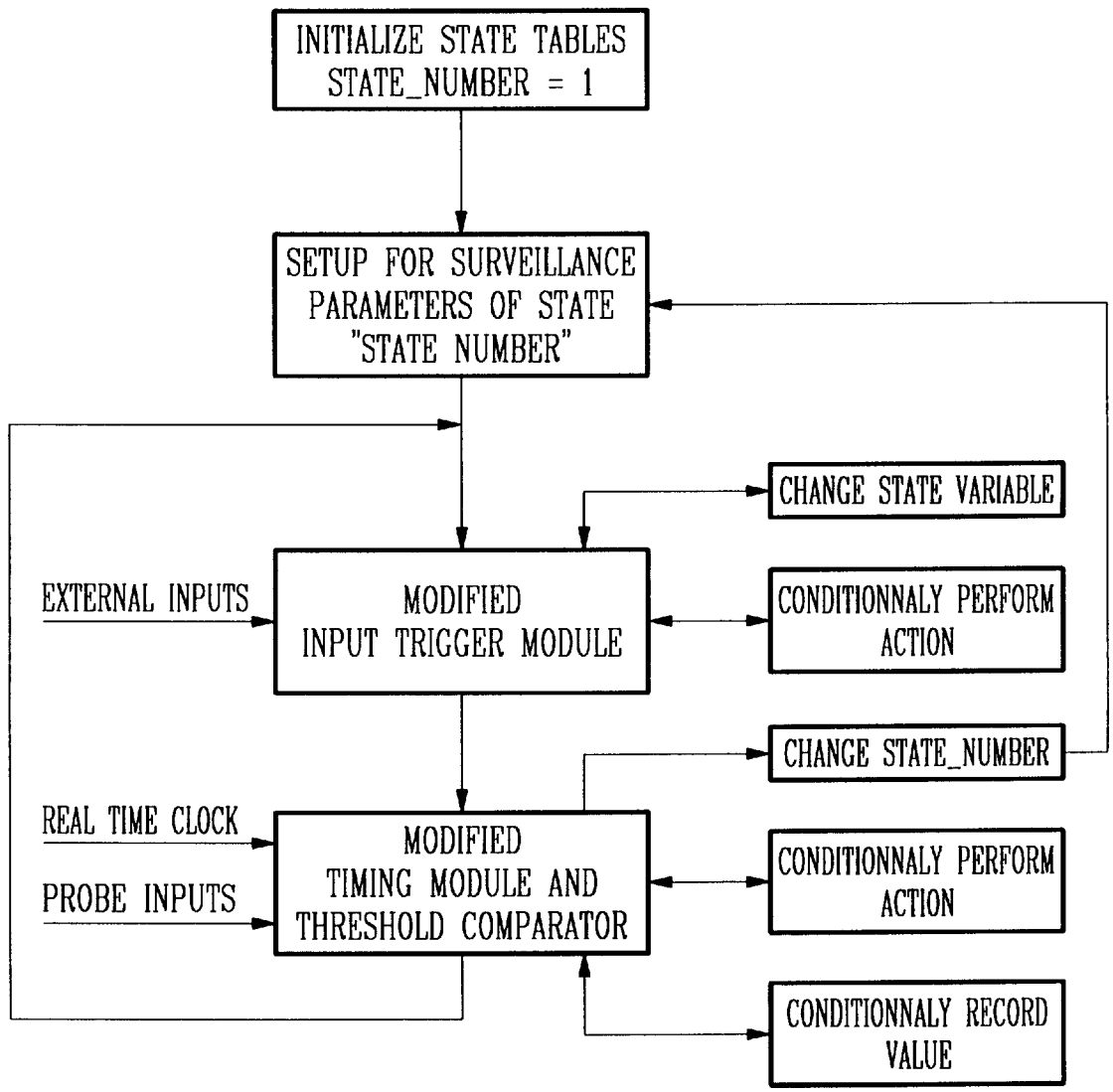
FIG_5

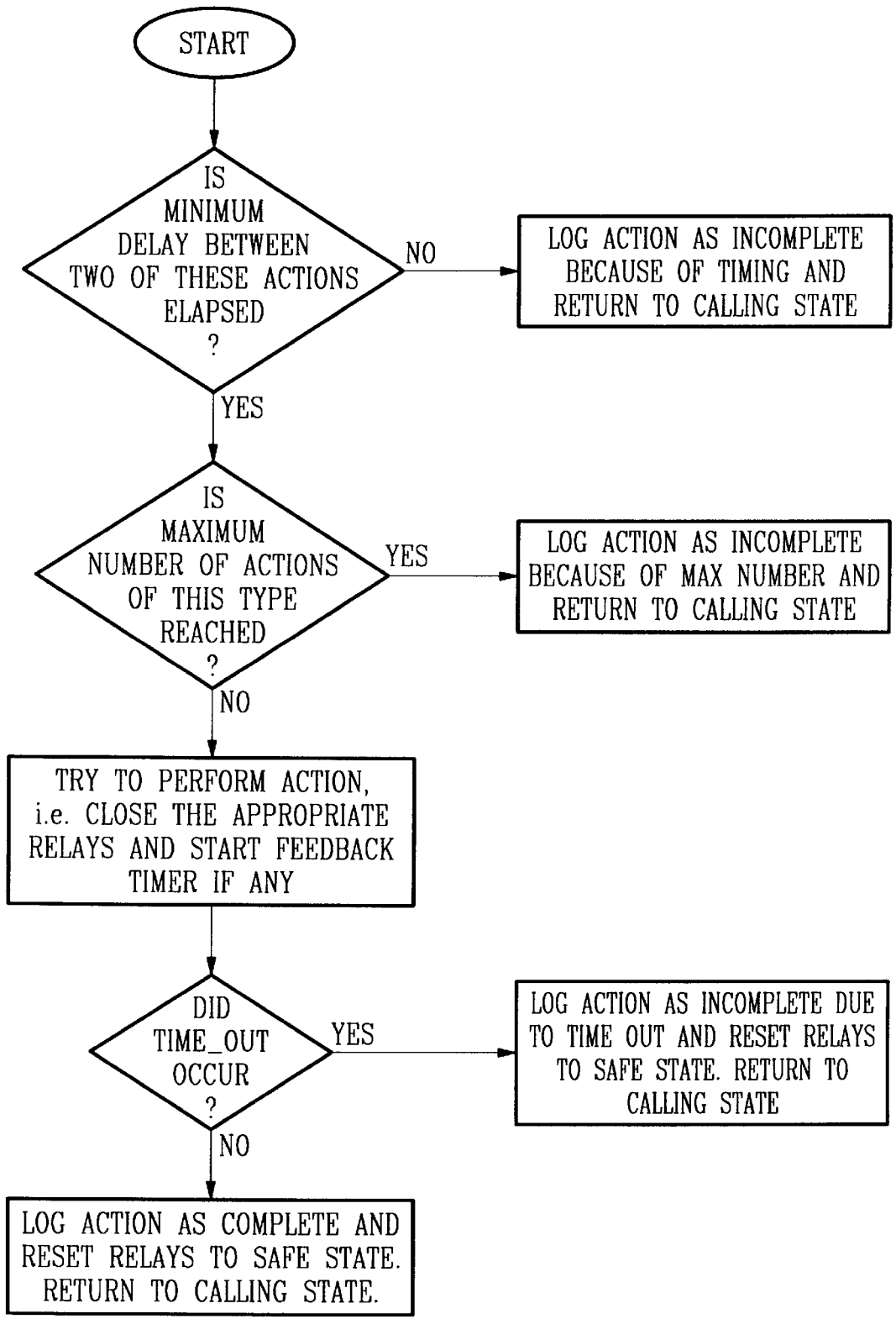

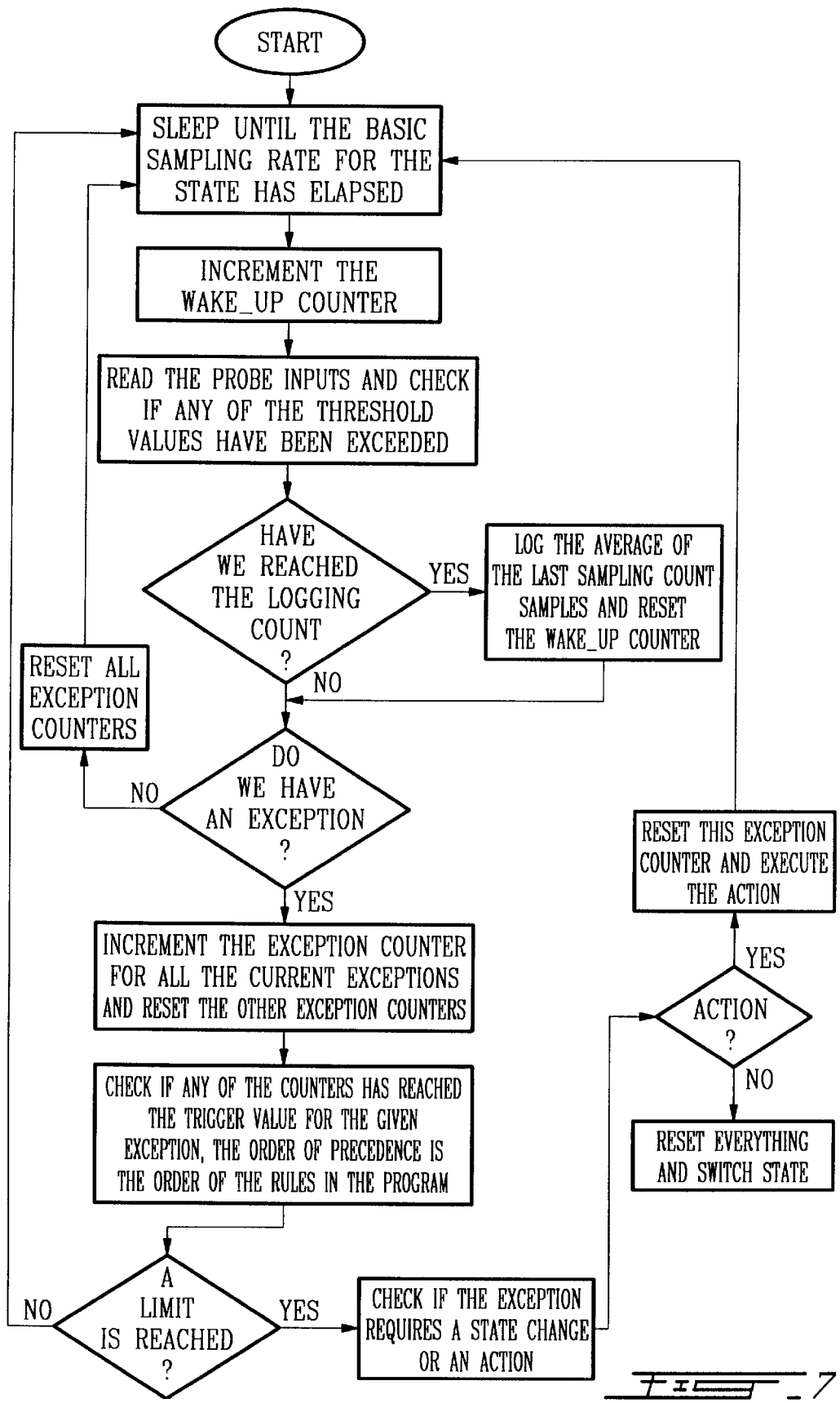

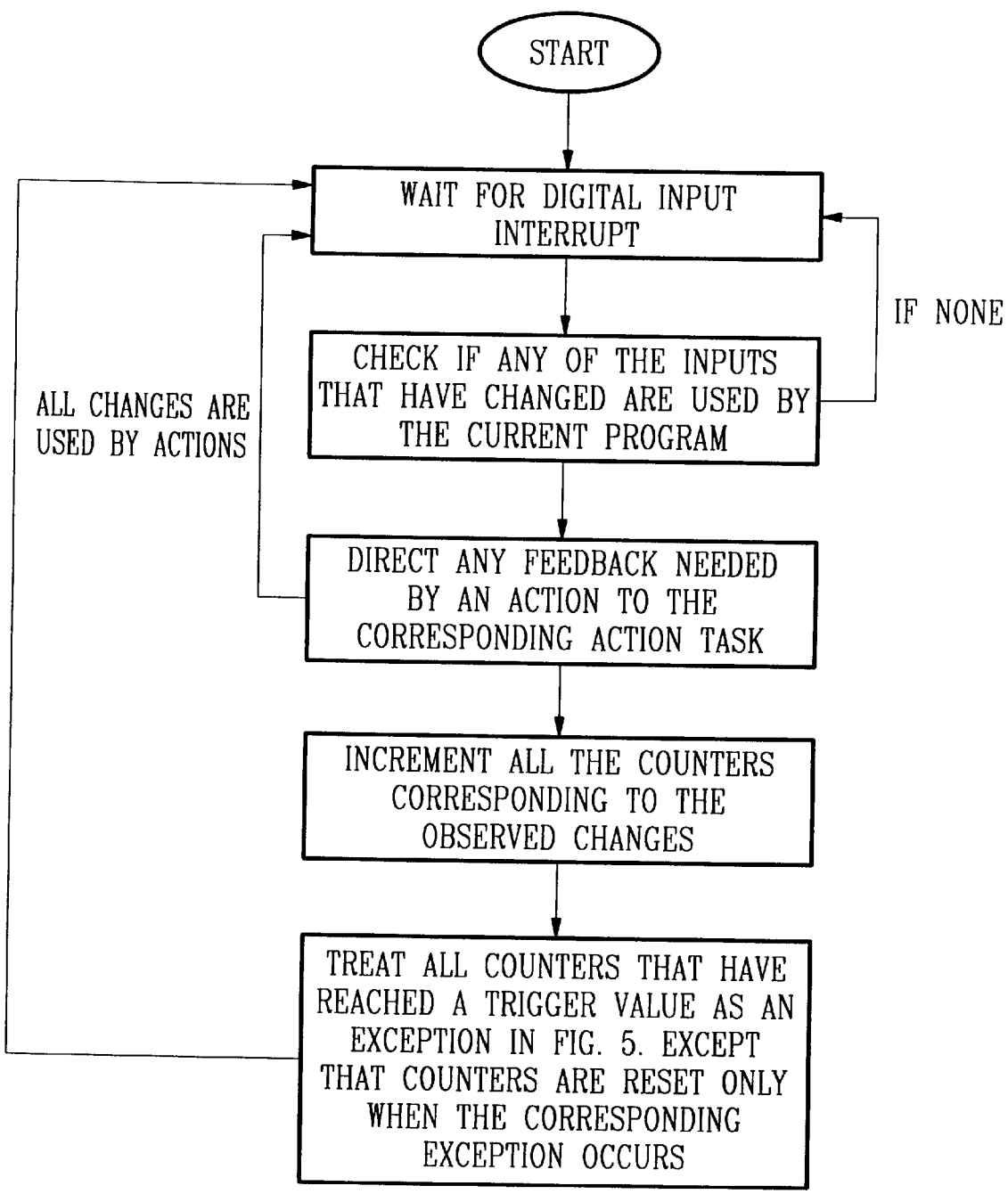

EFFLUENT MONITORING SYSTEM

FIELD OF THE INVENTION

The present invention relates to an effluent monitoring system. More particularly, the invention relates to an effluent monitoring system in which variable monitoring conditions can be set and dynamically changed.

BACKGROUND OF THE INVENTION

Traditionally, waste water quality monitoring was provided by lowering bottles, attached to a rope in the sewer to take samples. A few years ago, automatic samplers came on the market, driven by clocks and/or an external trigger. Today's machines, although often micro-computer driven, reflect their origins and are able to perform only very simple tasks. Typically they have probes that measure pH and temperature (parameters that appear in most by-laws on sewage), sometimes dissolved oxygen and conductivity; the output of these probes is either, via analog comparators, continuously compared to some preset threshold, or sampled through digital techniques for comparison with the digital equivalent of the mentioned thresholds.

To summarize the actual state of the art, water quality monitors can perform the following tasks:

Take a sample at a fixed interval by controlling a mechanical sampler;

Read and sometimes record the values of one or more probes at a fixed interval;

Take a sample when controlled by an external trigger (e.g. flow meter); and

Take a sample and/or record the value when one or more of the measured parameters exceed some threshold.

A typical embodiment of a state of the art system is the ISCO (T.M.) family of samplers and flow meters. In the 6700 model, for example, the sample frequency can be selected as:

From 1 min. to 59 h 59 min. in 1 min. increments between consecutive samples;

Non-uniform times in minutes or clock time;

Random time interval between consecutive samples;

From 1 to 9,999 flow pulses in single-pulse interval; and

Flow paced in volume with attachable flow module.

Optionally, one can add a pH module that can trigger samples when pH is outside a user provided range.

These systems are not well suited for long time base monitoring because, either they generate large amounts of monotonous data, or can ignore short term significant phenomena. Besides, the fixed threshold system can fill the sampler very fast, so that no bottles are available to receive interesting samples later on.

SUMMARY OF THE INVENTION

It is therefore an object of the present invention to provide an effluent monitoring system which overcomes the drawbacks associated with the prior art.

According to a first broad aspect of the present invention, an effluent monitoring system is provided in which a plurality of threshold values can be programmed, and the threshold values for probe inputs can be changed in response to a first condition.

According to a second broad aspect of the present invention, there is provided an effluent monitoring system which provides a variable and dynamic response to the effluent property detecting probe inputs for controlling a sampler device, alarm or the like.

According to a first aspect of the present invention, there is provided an effluent monitoring system for generating an action perform signal for controlling a sampler device or an alarm, the system comprising: a plurality of probe inputs receiving signals from a plurality of effluent property detecting probes; a memory storing a state number value and a plurality of monitoring parameter sets, each of the said sets corresponding to a value of the state number value and comprising: at least one threshold value associated with one of the probe input signals; a delay trigger time associated with each of the said threshold values; and an action parameter associated with each of the said threshold values; sampling means for reading the probe input signals at a sampling interval and for recording probe input values from the signals read; and comparator means for reading one of the sets corresponding to the state number value, and for interpreting the action parameter of the corresponding set to at least one of: a) change the state number value; and b) output an action perform signal based on information contained in the action parameter, if one of the probe input values read exceeds the at least one threshold value for the delay trigger time associated with the threshold value for the corresponding set, whereby a variable and dynamic response to the effluent property detecting probe inputs for controlling a sampler device, alarm or the like is provided.

According to a further aspect of the present invention, there is provided an effluent monitoring system comprising: a plurality of probe inputs receiving signals from a plurality of effluent property detecting probes; sampling means for reading the probe input signals at a sampling interval and for recording probe input values from the signals read at a recording frequency corresponding to a multiple of the sampling interval; and comparator means for comparing one of the said probe input values read to at least one corresponding threshold value and for increasing the recording frequency when the one of the probe input values read exceeds at least one corresponding threshold value, whereby better recording resolution is achieved when required.

The invention also provides an effluent monitoring system comprising: a plurality of probe inputs receiving signals from a plurality of effluent property detecting probes; sampling means for reading the probe input signals at a sampling interval and for recording probe input values from the signals read at a recording frequency corresponding to a multiple of the sampling interval; and comparator means for comparing one of the said probe input values read to at least one corresponding threshold value and for decreasing the sampling interval when the said one of the probe input values read exceeds at least one corresponding threshold value, whereby better sampling resolution is achieved when required.

BRIEF DESCRIPTION OF THE DRAWINGS

The invention will be better understood by way of the following detailed description of a preferred embodiment with reference to the appended drawings in which:

FIG. 5 is a flow diagram for the effluent monitoring system according to the preferred embodiment;

FIG. 6 is a flow diagram illustrating the steps involved in a conditional action according to the preferred embodiment;

FIG. 7 is a flow diagram illustrating the steps involved in monitoring a threshold value and a delay trigger time according to the preferred embodiment; and FIG. 8 is a flow diagram illustrating a main difference between the modified input trigger module and the timing/threshold module according to the preferred embodiment.

DETAILED DESCRIPTION OF THE PREFERRED EMBODIMENT

Figure 1:
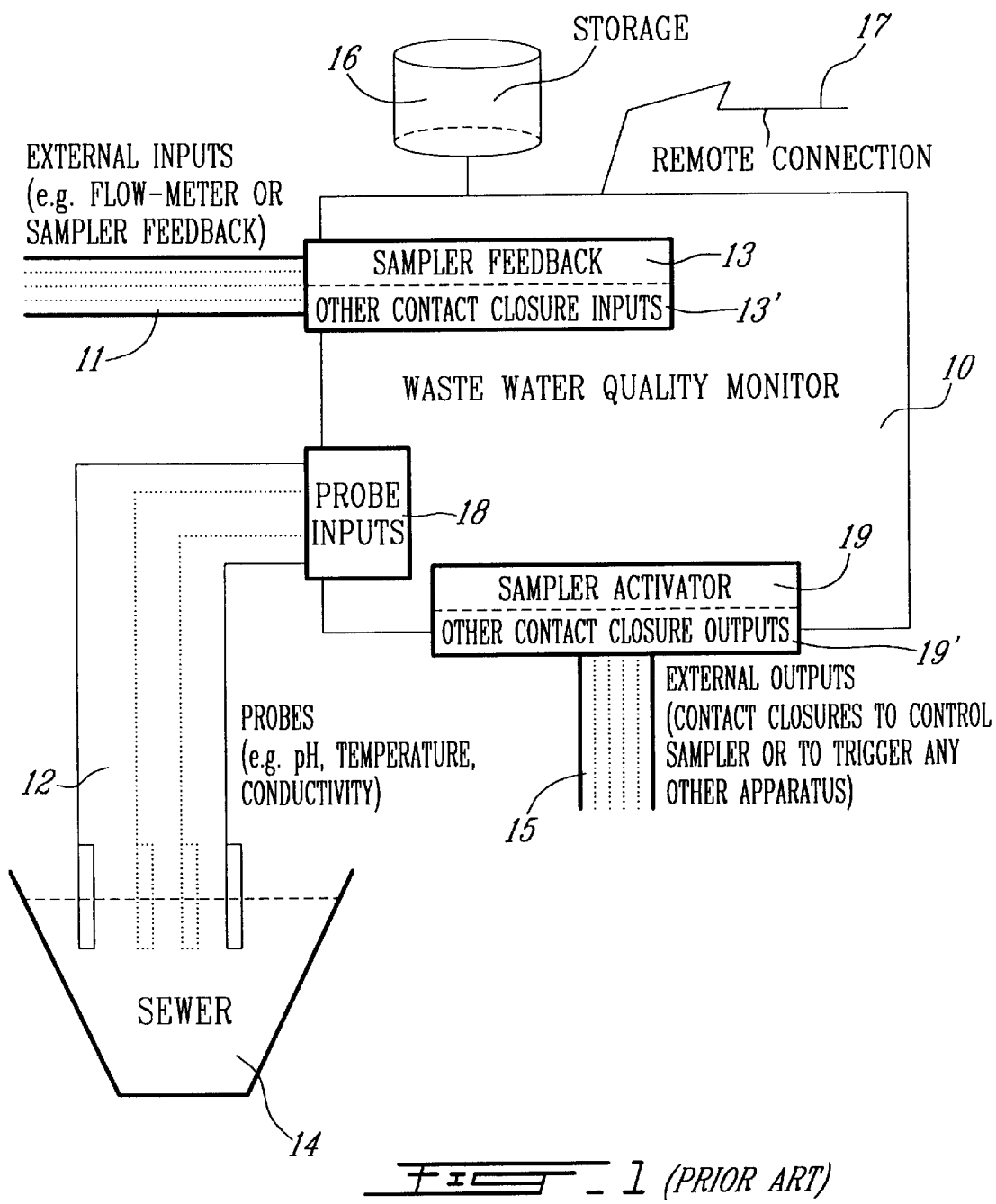
FIG. 1 illustrates an effluent monitoring system according to the prior art.

In the prior art systems, a waste water quality monitor 10, as illustrated in FIG. 1, is connected to a plurality of probe inputs 18 for receiving signals from a plurality of effluent property detecting probes 12 such as temperature, conductivity and pH, the latter being in contact with the effluent, as for example, being transported by a sewer 14. Further probe inputs from effluent property state detecting devices may also be used, such as flow meter inputs or effluent level gauge inputs. Such external inputs are shown in FIG. 1 by reference numeral 11. The monitor 10 records data on a mass storage device 16, such as a non-volatile memory device or a durable printer. Storage devices such as a magnetic tape device or a hard disk drive have been found to be insufficiently reliable in the field where they are subject to extreme temperatures, moisture and humidity. External outputs 15 to contact closures to control sampler devices are also provided and controlled by a sampler activator 19 and a contact closure activator 19' for other devices. These external outputs 15 may also be used to control local alarms or trigger other apparatus. Typically, some form of remote connection 17 is also provided to trigger a remote alarm.

Figure 2:
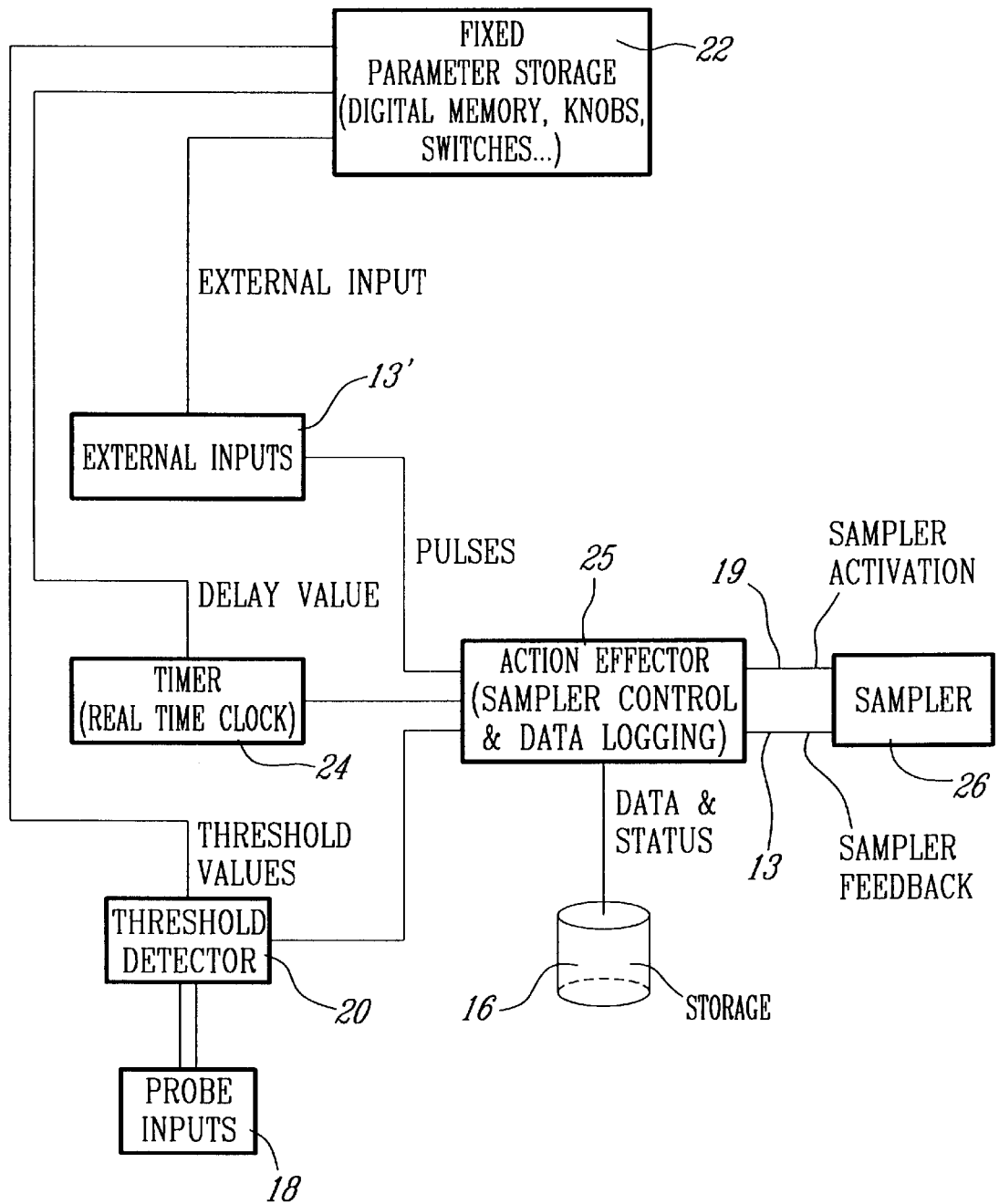
FIG. 2 illustrates a block diagram of an effluent monitoring system according to the prior art.

As shown in FIG. 2, the control system according to the prior art includes some form of fixed parameter storage such as digital memory, knobs and switches as shown by reference numeral 22. A threshold detector 20 compares the probe inputs 18 to various thresholds as set in the fixed parameter storage 22 and outputs a signal to a device 25 for controlling a sampler 26 and for recording in a log the time of taking the samples for storage in 16. A timer device and real time clock 24 provides a time signal to device 25 and can also activate the taking of a sample when a given delay value as set by the parameter storage 22 has elapsed. Other inputs 13' can be enabled or disabled according to the fixed parameter storage device 22 and the pulses from the external inputs, if enabled, are passed on to the effector 25.

Figure 4:
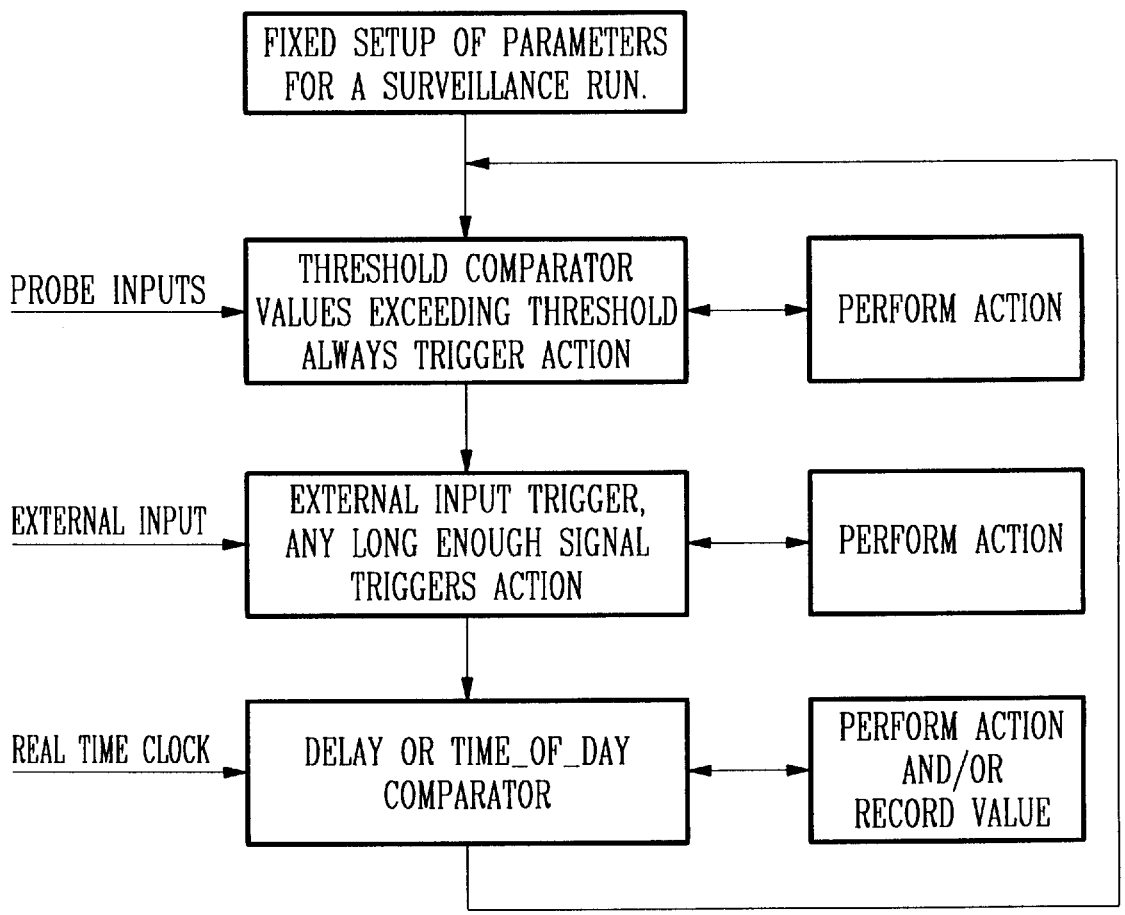
FIG. 4 is a flow diagram for an effluent monitoring system according to the prior art.

As illustrated in FIG. 4, in the known monitoring systems, the first step is to fix the parameters for a surveillance run. Based on these parameters, the probe inputs as well as the external inputs are compared to threshold values and the real time clock is compared to a certain elapsed time value or to a time of day value in order to trigger the taking of a sample, sounding of an alarm and/or the recording of an action or a value of a probe input. In the case of the external inputs coming from flow meters and the like, it may be that such signals are only generated when the effluent property being detected is above a certain threshold, and therefore, as shown in FIG. 4, an action may be performed when an external input trigger signal is generated for any sufficient period of time.

Figure 3:
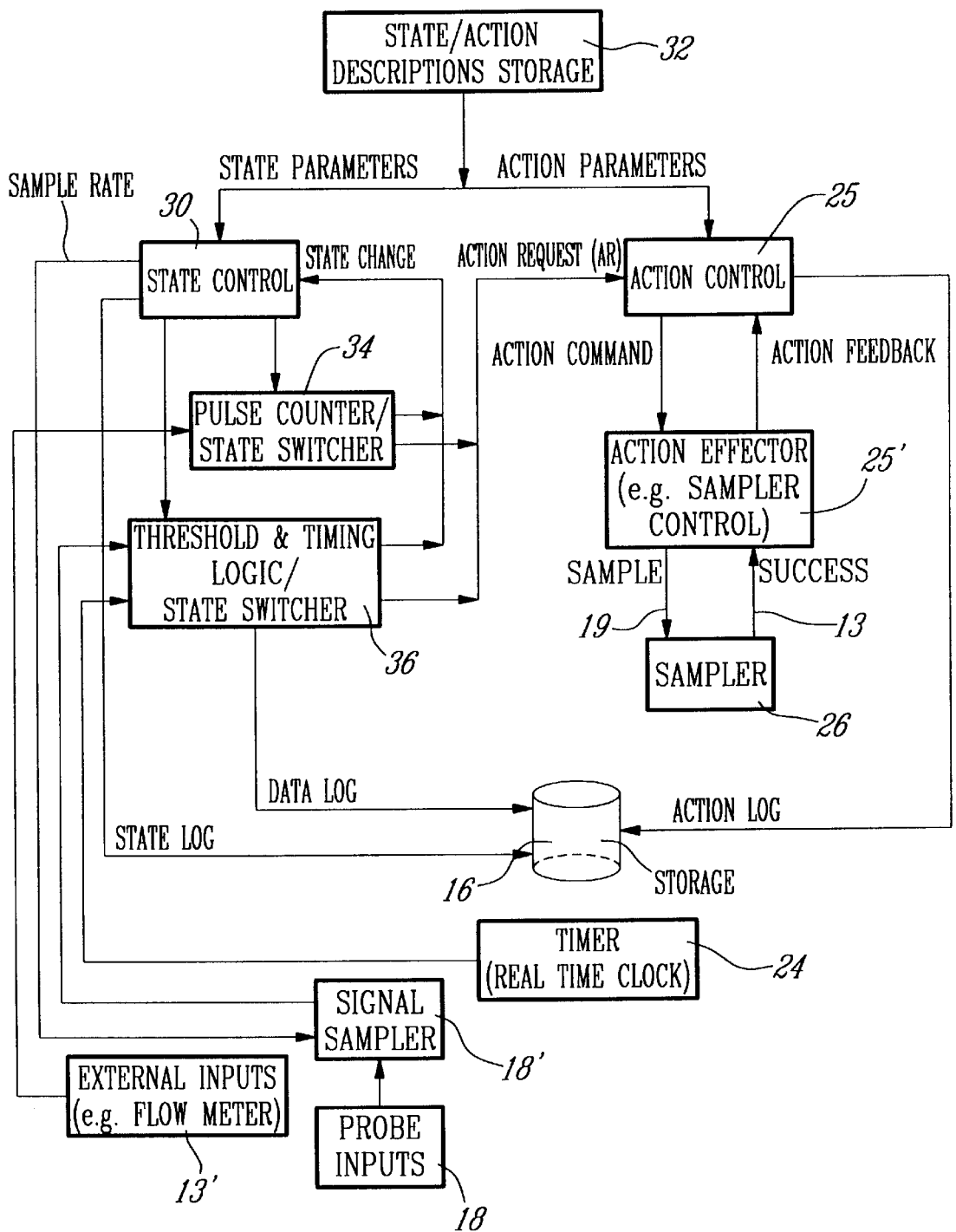
FIG. 3 illustrates a block diagram of the effluent monitoring system according to the preferred embodiment.

FIG. 3 illustrates the preferred embodiment of the present invention. A memory 32 stores a plurality of parameter sets corresponding to a state number. Each parameter set contains a minimum and a maximum threshold value for each of the probe input signals, as well as a delay trigger time associated with each of the threshold values, and an action parameter associated with each threshold value. In the state control device 30, a memory stores a state number and there is provided the necessary control to output to the the threshold and timing logic and state switcher device 36, and to the pulse counter state switcher 34, the appropriate threshold and delay trigger time values. The sample rate for the state is output to the signal sampler 18'. Should other device 34 or 36 decide that one of the threshold values has been exceeded (this includes being below a minimum threshold value), then the appropriate action according to the action parameter is signaled. The action parameter may indicate that the action control device 25 should be commanded to activate one of the sampler devices to take a sample of the effluent, or that the action control device should send a signal over line 17 to a remote alarm, or the action parameter may indicate that merely the state number value is to be changed, which device 34 or device 36 signals to the state control module 30. Of course, a sample may be taken when a given probe input signal exceeds the threshold and subsequent to the completion of the action, a change in the state number value may be signaled.

As will be appreciated, the action control device interacts with an action effector 25' connected to the sampler devices 26 in such a way that there is feedback to the action control to confirm that the samplers are properly operating. Failure to operate may result in an alarm being generated.

The storage device 16 records over time the values of the probe inputs over time as outputted by devices 34 and 36 along with the value of the state number. The action control device 25 also records its own activities in an activity log.

As will be appreciated, the signal sampler 18' reads the probe input signals 18 at a sampling interval. Devices 34 and 36 are responsible for recording the probe input signals read at a predetermined recording frequency. In the preferred embodiment, one of the monitoring parameters in the sets of monitoring parameters is the sampling rate value as well as the recording rate value or the recording frequency. Since the external inputs 13' are of the make or break type, a pulse indicative of the external input is transmitted to the pulse counter/state switcher 34, without requiring a sampling rate.

In the preferred embodiment, the various devices 30, 32, 34 and 36 can be provided by suitable software in a microcomputer. The software in the microcomputer also carries out the action control functions of device 25 in the preferred embodiment. FIG. 5 illustrates the overall flow of the logic in the software according to the preferred embodiment. FIG. 6 illustrates in greater detail the main steps involved in performing a conditional action. FIG. 7 illustrates in greater detail the steps involved in the software module providing the function of device 36. FIG. 8 illustrates in greater detail the main steps involved in the software module of device 34.

Although in the preferred embodiment the comparator means in device 36 respond simply to the magnitude of the probe input signals read, it is also contemplated according to the present invention to respond to variations in the probe input values read, for example, the first time derivative of the probe input signals could be monitored to cause a state change resulting in a change in the sampling rate or the recording rate or frequency. This has the advantage that as long as the signal level is stable, the sampling rate and recording rate need not be very high, whereas as soon as there is activity in the signal being detected, greater sampling or recording can be carried out.

As can be appreciated, device 36 may signal a state change or action request purely as a function of time. The measurement of time may be a simple measurement of the length of time spent in a particular state, or it may be a function of time of day.

EXAMPLE

In the following, an example of the effluent monitoring system according to the preferred embodiment in operation is given. The plurality of probe inputs are acidity (PH), temperature (TP) and effluent conductivity (CD). A flow meter input in not included in this example. In the following tables six states are described.

TABLE 1

State number: S01
State Name: Sampling
Measurement period: 10 seconds
Measurement period: 10 seconds
Number of measurements per recording: 30
State Change Conditions

| Type | Count | Next State | Var. | Op | Value 1 | Value 2 |
|------|-------|------------|------|-----|---------|---------|
| Meas. | 24 | S02 | PH | <= | 6 | |
| Meas. | 24 | S02 | PH | > | 10.5 | |
| Meas. | 24 | S02 | TP | > | 40 | |
| Meas. | 24 | S02 | TP | > | 40 | |

TABLE 2

State number: S02
State Name: Alarm
Measurement period: 10 seconds
Number of measurements per recording: 1
State Change Conditions

| Type | Count | Next State | Var. | Op | Value 1 | Value 2 |
|------|-------|------------|------|-----|---------|---------|
| Meas. | 6 | S04 | PH | <= | 6 | |
| Meas. | 6 | S05 | PH | > | 10.5 | |
| Meas. | 6 | S06 | TP | > | 40 | |
| Meas. | 6 | S03 | CD | > | 5 | |
| Meas. | 2 | S01 | PH | () | 6.01 | 10.49 |
| | | | CD | <= | 4.99 | |
| | | | TP | <= | 39.99 | |

TABLE 3

State number: S03
State Name: Take Sample CD
Measurement period: 5 seconds
Number of measurements per recording: 1
State Change Conditions

| Type | Count | Next State | Var. | Op | Value 1 | Value 2 |
|------|-------|------------|------|-----|---------|---------|
| Delay | | A04 | | | 00:00:05 | 00:00:00 |
| Delay | | S01 | | | 00:02:00 | 00:00:00 |

TABLE 4

State number: S04
State Name: Take Sample Low pH
Measurement period: 5 seconds
Number of measurements per recording: .1
State Change Conditions

| Type | Count | Next State | Var. | Op | Value 1 | Value 2 |
|------|-------|------------|------|-----|---------|---------|
| Delay | | A01 | | | 00:00:05 | 00:00:00 |
| Delay | | S01 | | | 00:02:00 | 00:00:00 |

TABLE 5

State number: S05
State Name: Take Sample High pH
Measurement period: 5 seconds
Number of measurements per recording: 1
State Change Conditions

| Type | Count | Next State | Var. | Op | Value 1 | Value 2 |
|------|-------|------------|------|-----|---------|---------|
| Delay | | A02 | | | 00:00:05 | 00:00:00 |
| Delay | | S01 | | | 00:02:00 | 00:00:00 |

TABLE 6

State number: S06
State Name: Take Sample Temperature
Measurement period: 5 seconds
Number of measurements per recording: 1
State Change Conditions

| Type | Count | Next State | Var. | Op | Value 1 | Value 2 |
|------|-------|------------|------|-----|---------|---------|
| Delay | | A03 | | | 00:00:05 | 00:00:00 |
| Delay | | S01 | | | 00:02:00 | 00:00:00 |

As will be appreciated, there are only two main states in this simple example. The first state S01 has a measurement period which is long (10 s) and a recording period which is very long, namely every 30 measurements or every 300 seconds. The low frequency of measurement and recording saves on power requirements for the system, which is important for battery powered systems installed in the field. If the pH rises above 10.5 or drops below 6 for 24 measurements (i.e. 240 seconds), then the system proceeds to operate with the parameters of state S02. The same holds true for temperature exceeding 40° C. and conductivity exceeding 5 cm/ohm.

State S02 is called the alarm state because an abnormal situation has been detected. While sampling continues every 10 seconds, every measurement is recorded and better resolution of the changing effluent conditions is obtained for later analysis. If the pH, temperature or conductivity condition persists for an additional minute (six counts of 10 seconds), then the system operates with the parameters of states S03 through S06. If the pH range, conductivity and temperature all return to normal for two counts, then the system operates with the parameters of state S01.

The states S03 to S06 are temporary states of the system during which an action is requested and then the system returns to the first state after 2 minutes. The parameter sets include only delay conditions and no measured effluent property responsive condition.

The preceding description of the preferred embodiment of the invention is merely one example of how the invention may be put into practice and is not intended to limit the scope of the invention as defined in the appended claims.

I claim:

1. An effluent monitoring system for generating an action perform signal for controlling a sampler device or an alarm, said system comprising:
   a plurality of probe inputs receiving signals from a plurality of effluent property detecting probes;
   a memory storing a state number value and a plurality of monitoring parameter sets, each said set corresponding to a value of said state number value and comprising:
   at least one threshold value associated with one of said probe input signals;

a delay trigger time associated with each said threshold value; and an action parameter associated with each said threshold value;

sampling means for reading said probe input signals at a sampling interval and for recording probe input values from said signals read; and comparator means for reading one of said sets corresponding to said state number value, and for interpreting said action parameter of said corresponding set to at least one of: a) change said state number value; and b) output an action perform signal based on information contained in said action parameter, if one of said probe input values read exceeds said at least one threshold value for said delay trigger time associated with said threshold value for said corresponding set, whereby a variable and dynamic response to the effluent property detecting probe inputs for controlling a sampler device, alarm or the like is provided.

2. The system as claimed in claim 1, wherein said monitoring parameter sets each comprise a sampling rate value, and said sampling interval is equal to a sampling rate value of one of said sets corresponding to said state number value.

3. The system as claimed in claim 1, further comprising recording means for recording at least some of said probe input values read.

4. The system as claimed in claim 3, wherein at least some of said monitoring parameter sets each comprise a recording rate value, and said recording means record said at least some of said probe input values read at intervals specified by said recording rate value.

5. The system as claimed in claim 2, further comprising recording means for recording at least some of said probe input values read.

6. The system as claimed in claim 5, wherein at least some of said monitoring parameter sets each comprise a recording rate value, and said recording means record said at least some of said probe input values read at intervals specified by said recording rate value.

7. The system as claimed in claim 1, wherein said monitoring parameter sets further include at least one further set of parameters comprising:

a delay trigger time; and an action parameter associated with said delay trigger time.

8. The system as claimed in claim 7, wherein said delay trigger time associated with said at least one further set of parameters is a fixed interval.

9. The system as claimed in claim 7, wherein said delay trigger time associated with said at least one further set of parameters corresponds to a given date and hour.

10. The system as claimed in claim 1, wherein one of said threshold value associated with one of said probe input signals for at least one of said sets is within a normal range of said corresponding probe input value, and said delay trigger time associated with said one threshold value is a fixed interval.

11. The system as claimed in claim 1, wherein one of said threshold value associated with one of said probe input signals for at least one of said sets is within a normal range of said corresponding probe input value, and said delay trigger time associated with said one threshold value corresponds to a given date and hour.

12. The system as claimed in claim 1, wherein said comparator means interpret said action parameter of said corresponding set to at least one of: a) change said state number value; and b) output an action perform signal based on information contained in said action parameter, if at least two of said probe input values read all exceed corresponding ones of said at least one threshold value for said corresponding set, whereby a logical conjunction of a comparison of probe values with different thresholds is responded to.

13. An effluent monitoring system comprising:

a plurality of probe inputs receiving signals from a plurality of effluent property detecting probes;

sampling means for reading said probe input signals at a sampling interval and for recording probe input values from said signals read at a recording frequency corresponding to a multiple of said sampling interval; and comparator means for comparing one of said probe input values read to at least one corresponding threshold value and for increasing said recording frequency when said one of said probe input values read exceeds at least one corresponding threshold value, whereby better recording resolution is achieved when required.

14. An effluent monitoring system comprising:

a plurality of probe inputs receiving signals from a plurality of effluent property detecting probes;

sampling means for reading said probe input signals at a sampling interval and for recording probe input values from said signals read at a recording frequency corresponding to a multiple of said sampling interval; and comparator means for comparing one of said probe input values read to at least one corresponding threshold value and for decreasing said sampling interval when said one of said probe input values read exceeds at least one corresponding threshold value, whereby better sampling resolution is achieved when required.

15. The system as claimed in claim 13, wherein said comparator means compare a first time derivative of said one of said probe input values read to said at least one corresponding threshold value, whereby said recording frequency increases when there is change in said one of said probe input values read.

16. The system as claimed in claim 14, wherein said comparator means compare a first time derivative of said one of said probe input values read to said at least one corresponding threshold value, whereby said sampling interval decreases when there is change in said one of said probe input values read.

17. The system as claimed in claim 15, wherein said comparator means controls said recording frequency to be a function of said first derivative.

18. The system as claimed in claim 16, wherein said comparator means controls said sampling interval to be a function of said first derivative.

* * * * *